United States Patent
Groth et al.

(10) Patent No.: US 11,468,567 B2
(45) Date of Patent: Oct. 11, 2022

(54) DISPLAY OF MEDICAL IMAGE DATA

(71) Applicant: KONINKLIJKE PHILIPS N. V., Eindhoven (NL)

(72) Inventors: Alexandra Groth, Hamburg (DE); Axel Saalbach, Hamburg (DE); Rolf Jürgen Weese, Norderstedt (DE)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 93 days.

(21) Appl. No.: 16/977,538

(22) PCT Filed: Feb. 25, 2019

(86) PCT No.: PCT/EP2019/054506
§ 371 (c)(1),
(2) Date: Sep. 2, 2020

(87) PCT Pub. No.: WO2019/170443
PCT Pub. Date: Sep. 12, 2019

(65) Prior Publication Data
US 2021/0004960 A1    Jan. 7, 2021

(30) Foreign Application Priority Data

Mar. 7, 2018   (EP) .................................... 18160406

(51) Int. Cl.
*G06K 9/00* (2022.01)
*G06T 7/00* (2017.01)
(Continued)

(52) U.S. Cl.
CPC .......... *G06T 7/0014* (2013.01); *A61B 5/7267* (2013.01); *A61B 5/743* (2013.01);
(Continued)

(58) Field of Classification Search
CPC ........ G16H 50/50; G16H 40/63; G16H 20/40; G16H 70/20; G16H 30/20; G16H 15/00;
(Continued)

(56) References Cited

U.S. PATENT DOCUMENTS

2008/0267471 A1   10/2008   Yu et al.
2012/0184845 A1 *  7/2012   Ishikawa ................ A61B 3/102
                                                              600/425
(Continued)

FOREIGN PATENT DOCUMENTS

CN         101799937 A       8/2010
WO         2018015414 A1     1/2018

OTHER PUBLICATIONS

International Search and Written Opinion for International Application No. PCT/EP2019/054506, filed Feb. 25, 2019, 17 pages.
(Continued)

*Primary Examiner* — Alex Kok S Liew
(74) *Attorney, Agent, or Firm* — Micah-Shalom Kesselman (57) ABSTRACT

A system and method are provided for display of medical image data, with the display of the medical image data being determined on the basis of schematic image data of a schematic representation of an anatomical structure. The schematic representation may provide a particular view of the anatomical structure. The type of anatomical structure and the view of the anatomical structure provided by the schematic representation may be determined based on one or more image features in the schematic image data. The view may be characterized as a geometrically-defined perspective at which the anatomical structure is shown in the schematic representation. An output image may be generated showing the anatomical structure in the medical image data in accordance with said determined geometrically-defined perspective. A user may thus be provided with a display of medical
(Continued)

image data which is easier to interpret having considered said schematic representation.

13 Claims, 5 Drawing Sheets

(51) Int. Cl.

| | | |
|---|---|---|
| *G06T 7/10* | (2017.01) | |
| *G06T 7/70* | (2017.01) | |
| *G16H 50/50* | (2018.01) | |
| *G16H 15/00* | (2018.01) | |
| *G16H 30/20* | (2018.01) | |
| *G16H 30/40* | (2018.01) | |
| *G06N 20/00* | (2019.01) | |
| *A61B 5/00* | (2006.01) | |
| *G06K 9/62* | (2022.01) | |
| *G06T 15/20* | (2011.01) | |

(52) U.S. Cl.
CPC .......... *A61B 5/7475* (2013.01); *G06K 9/6256* (2013.01); *G06K 9/6267* (2013.01); *G06N 20/00* (2019.01); *G06T 7/10* (2017.01); *G06T 7/70* (2017.01); *G06T 15/20* (2013.01); *G16H 15/00* (2018.01); *G16H 30/20* (2018.01); *G16H 30/40* (2018.01); *G16H 50/50* (2018.01); *A61B 2576/00* (2013.01); *G06T 2200/24* (2013.01); *G06T 2207/20081* (2013.01); *G06T 2207/30004* (2013.01)

(58) Field of Classification Search
CPC ........ G16H 50/20; G16H 30/40; G16H 10/20; G16H 20/10; G16H 70/60; G16H 10/60; G16H 40/20; G16H 40/60; G16H 40/67; A61B 34/01; A61B 34/00; A61B 5/055; A61B 2034/104; A61B 2034/105
See application file for complete search history.

(56) References Cited

U.S. PATENT DOCUMENTS

| | | | |
|---|---|---|---|
| 2013/0336553 A1* | 12/2013 | Buisseret | G06T 7/60 382/128 |
| 2016/0035093 A1 | 2/2016 | Kateb et al. | |
| 2016/0217318 A1 | 7/2016 | Hayasaka | |
| 2017/0116497 A1 | 4/2017 | Georgescu et al. | |
| 2017/0116748 A1 | 4/2017 | Scutura et al. | |
| 2017/0161590 A1 | 6/2017 | Boulkenafed et al. | |
| 2018/0065248 A1* | 3/2018 | Barral | G05B 13/04 |
| 2019/0188852 A1* | 6/2019 | Reicher | G06N 5/022 |

OTHER PUBLICATIONS

Jing, et al., "A Novel Medical Freehand Sketch 3D Model Retrieval Method by Dimensionality Reduction and Feature Vector Transformation", Hindawi Publishing Corporation, Computational and Mathematical Methods in Medicine, vol. 2016, Article ID 4738391, pp. 1-11.

Yasseen, et al., "View selection for sketch-based 3D model retrieval using visual part shape description", Visual Computer, Springer Verlag, 2017, 33 (5), pp. 565-583.

Zhao, et al., "Learning best views of 3D shapes from sketch contour", The Visual Computer, International Journal of Computer Graphics, Jun. 2015, vols. 31, No. 6-8, pp. 1-10.

* cited by examiner

DISPLAY OF MEDICAL IMAGE DATA

RELATED APPLICATIONS

This application is the U.S. National Phase application under 35 U.S.C. § 371 of International Application No. PCT/EP2019/054506, filed on Feb. 25, 2019, which claims priority to and the benefit of European Application Serial No. 18160406.7, filed Mar. 7, 2018. These applications are hereby incorporated by reference herein, for all purposes.

FIELD OF THE INVENTION

The invention relates to a system and a computer-implemented method for display of medical image data.

The invention further relates to a workstation and imaging apparatus comprising the system, and to a computer-readable medium comprising instructions for causing a processor system to perform the computer-implemented method.

BACKGROUND OF THE INVENTION

In the medical field, once a patient has been diagnosed and/or treatment has been performed, it is customary for a physician to write a medical report summarizing the diagnosis and/or treatment. For example, a medical abnormality, such as a lesion, may have been diagnosed and/or treated. The medical abnormality may have been determined from medical image data acquired of the patient before or during diagnosis and/or treatment.

The report may frequently contain a schematic representation of the anatomical structure to which the medical abnormality pertains, and which may be annotated to identify the location of the medical abnormality.

There are various reasons for using such a schematic representation in medical reporting, including its suitability for being reproduced on paper, e.g., enabling the physician to simply mark the medical abnormality on a predefined 'template' schematic representation of an anatomical structure. Another reason may be that a schematic representation is easy to interpret and/or easy to annotate.

While a recipient of the report may find the schematic representation to be helpful, he/she may still desire to view medical image data of the patient, e.g., to verify a diagnosis in the originally acquired medical image data of the patient, or to verify the progress of the treatment in later acquired medical image data.

SUMMARY OF THE INVENTION

Disadvantageously, a schematic representation in a report is typically not digitally linked to the medical image data, e.g., by way of a hyperlink or similar measure. Accordingly, it may be cumbersome for the physician or other type of user to retrieve the associated medical image data. Moreover, even if such a digital link were to be provided, the medical image data may be difficult to mentally match to the schematic representation and thus may be difficult to interpret for the user.

It would be advantageous to obtain a system and method which provides a user with a display of medical image data of a patient which is easier to interpret having considered the schematic representation.

In accordance with a first aspect of the invention, a system is provided for display of medical image data, comprising:
an input interface for accessing first image data comprising a schematic representation of an anatomical structure, the schematic representation providing a particular view of the anatomical structure;
a memory comprising instruction data representing a set of instructions;
a processor configured to communicate with the input interface and the memory and to execute the set of instructions, wherein the set of instructions, when executed by the processor, cause the processor to:
analyze the first image data to determine i) a type of anatomical structure and ii) the view of the anatomical structure provided by the schematic representation, based on one or more image features in the first image data;
via the input interface, access second image data acquired of a patient, the second image data comprising the type of anatomical structure; and
generate an output image showing the anatomical structure in the second image data in accordance with said determined view.

A further aspect of the invention provides a workstation or imaging apparatus comprising the system.

A further aspect of the invention provides a computer-implemented method for display of medical image data, comprising:
accessing first image data comprising a schematic representation of an anatomical structure, the schematic representation providing a particular view of the anatomical structure;
analyzing the first image data to determine i) a type of anatomical structure and ii) the view of the anatomical structure provided by the schematic representation, based on one or more image features in the first image data;
accessing second image data acquired of a patient, the second image data comprising the type of anatomical structure; and
generating an output image showing the anatomical structure in the second image data in accordance with said determined view.

A further aspect of the invention provides a computer-readable medium comprising transitory or non-transitory data representing instructions arranged to cause a processor system to perform the computer-implemented method.

The above measures provide an input interface for accessing image data comprising a schematic representation of an anatomical structure. The schematic representation may be a line drawing, a contour drawing, etc., but may also take different forms which have a schematic character. Generally, the first image data does not represent the (direct) output of a medical imaging modality. In some embodiments, the first image data may represent a scan or photo of a paper version of the schematic representation. For example, a physician may have annotated a template schematic representation on paper which was then scanned or photographed so as to obtain the first image data. In other embodiments, the schematic representation may have been 'natively digital', e.g., may have been generated in the digital domain rather than having been scanned or photographed.

A processor is provided which is configurable by instructions stored in a memory to analyze the first image data to determine a type of the anatomical structure shown in the first image data. For example, the anatomical structure may be a tissue, a part of an organ, organ system, etc. The type of anatomical structure may then refer to the type of tissue (e.g., myocardium), the type of part of the organ (e.g., ventricle of the heart), the type of organ (e.g., heart), etc. In addition, it is determined which view of the anatomical structure is provided. Effectively, the view may be characterized by the processor, e.g., directly in terms of view parameters characterizing the view or indirectly by identifying the view so as to allow the one or more view parameters to be looked-up, with possible view parameters including the graphical perspective being provided of the anatomical structure (e.g., lateral, sagittal, or another type of geometrically defined perspective), a type of view (e.g., cross-sectional or exterior) but in some embodiments also which part of an anatomical cycle is shown by the view (e.g., the heart during systole or diastole).

To determine the type of anatomical structure and the view provided by the schematic representation of the anatomical structure, the processor uses one or more image features in the first image data. As will also be elucidated with reference to the embodiments, various options exist here. A non-limiting example is that, as image features, anatomical image features may be used such as anatomical landmarks which may be identified in the schematic representation. Another non-limiting example is that the first image data may comprise a code-based image feature, i.e., an image-based code, such as a barcode or QR code, which may directly identify the type of anatomical structure and the view, or at least allow these to be determined, e.g., based on a look-up in a database. In general, the term 'image feature' may refer to a feature which is directly contained in or may be determined from the image data, e.g., by image analysis or pattern recognition techniques.

Having determined the type of anatomical structure and the view, second image data is accessed which is acquired of a patient and which shows the same type of anatomical structure as shown in the schematic representation. This image data is in the following also simply referred to as 'medical image data', denoting that the second image data is acquired using a medical imaging modality such as Ultrasound, Computer Tomography (CT), Magnetic Resonance Imaging (MRI), etc. In many embodiments, the schematic representation may be associated with a patient, e.g., by being included in a medical report of the patient, and the medical image data may have been acquired from the same patient. For example, the system may access all image data from an electronic health record of a patient and thus as a rule access the first and second image data from the same patient.

The processor then generates an output image which shows the anatomical structure in the second image data in accordance with said determined view. Effectively, the output image may be generated such that one or more view characteristics associated with the visualization of the anatomical structure in the output image correspond to those of the visualization of the anatomical structure in the schematic representation. A non-limiting example is that if the schematic representation provides a lateral cross-section of the heart, the second image data may be processed so as to also provide a lateral cross-section of the heart in the output image. A specific yet non-limiting example is that if the second image data is volumetric image data, a multiplanar reformatting technique may be applied to the second image data so as to obtain the lateral cross-section of the heart.

The above measures have not only the effect that the user is provided with display of medical image data of a patient showing an anatomical structure on the basis of a schematic representation of the anatomical structure, but also that the visualization of the anatomical structure in the output image is brought into (closer) correspondence to the visualization of the anatomical structure in the schematic representation. Accordingly, it is not needed for the user to manually manipulate the display of the medical image data so as to obtain a view of the medical image data which corresponds to the view of the anatomical structure provided by the schematic representation. Accordingly, the number of user interactions between the user and the system may be reduced. The output image may also be inherently easier to interpret for the user having already considered the schematic representation.

Optionally, the schematic representation of the anatomical structure comprises an annotation, and the set of instructions cause the processor to:

detect an anatomical location of the annotation in the schematic representation of the anatomical structure; and based on said detected anatomical location, annotate the output image in correspondence with the annotation in the schematic representation.

Accordingly, an annotation in the schematic representation may be effectively 'transferred' from the schematic representation to the output image, as the system may provide an annotation at a same or similar anatomical location as the annotation in schematic representation. Since the annotation in the schematic representation may denote an anatomical location of relevance, e.g., a location of a lesion, the relevant location is indicated to the user without the user having to manually identify the relevant anatomical location in the output image.

Optionally, the set of instructions cause the processor to determine the type of anatomical structure and/or the view of the anatomical structure by:

via the input interface, accessing a database comprising i) image data of a set of schematic representations of anatomical structures and ii) metadata indicating for each schematic representation the type of anatomical structure and/or the view of the anatomical structure provided by the respective schematic representation; and comparing the first image data to the image data of each, or a subset of the set of schematic representations.

The type of anatomical structure may be identified by comparing the image data of the schematic representation to the image data of a set of reference schematic representations which may represent different types of anatomical structures and of which the type of anatomical structure is known from metadata. This provides an efficient manner of determining the type of anatomical structure. Additionally or alternatively, the view provided by the schematic representation may be identified in this manner, e.g., by the set of schematic representations providing different views of one or more types of anatomical structures, with characteristics of said views being known from metadata. Such comparison may in general be performed in various ways, for example by registering the first image data to the image data of each, or the subset of the set of schematic representations, e.g., using known image registration techniques, and determining a correspondence of said registered image data. The 'best' correspondence according to a correspondence criterion may then be selected as most probably representing the schematic representation at hand, with the associated metadata then identifying the type of anatomical structure and/or the view in the schematic representation.

Optionally, the set of instructions cause the processor to determine the type of anatomical structure and/or the view of the anatomical structure provided by the schematic representation by applying an image classification technique to the first image data. Image classification techniques are known per se, both inside and outside of the medical domain. Such image classification techniques may be at least in part based on heuristics. Additionally or alternatively, the image classification technique may be based on machine learning. A particular advantageous technique may be so-called deep learning, which has in recent years been found to produce results comparable to and in some cases superior to human experts.

For example, a machine learning-based image classification technique may be trained to identify a view provided by the schematic representation by:
- accessing a 3D model of the type of anatomical structure, such as a segmentation model for segmenting the type of anatomical structure;
- generating projections of the 3D model from different viewpoints, thereby obtaining a set of 2D images;
- using the 2D images and data characterizing the different viewpoints as training input to the image classification technique.

Effectively, the image classification technique may be trained on different projections of a 3D model of the type of anatomical structure, as such projections may resemble schematic representations of the anatomical structure. As the viewpoint, or in general view geometry, of each projection is known, e.g., as defined by one or more view parameters, the image classification technique may be trained to provide the one or more view parameters as output of the classification, or an identifier which allows the one or more view parameters to be looked-up.

In this respect, it is noted that the training may be performed by the system, in that the processor may be configured to perform the training. Alternatively, the image classification technique may have been trained using another system, e.g., a 'training system', and the claimed system may obtain data representing the trained image classification technique from said training system.

Optionally, the first image data comprises an image-based code indicative of the type of anatomical part and/or the view of the anatomical structure provided by the schematic representation, wherein the set of instructions cause the processor to analyze the first image data to identify the image-based code.

Alternatively or additionally to using the image data of the schematic representation of the anatomical structure itself, e.g., in the form of contours, anatomical landmarks, etc., the first image data may be provided with an image-based code, such as a barcode, a QR code, a number, a string, etc., which may be identified by the system and which may directly identify the type of anatomical structure and/or the view, or at least allow these to be determined, e.g., based on a look-up in a database. For example, the schematic representation may represent a 'template' schematic representation which may be annotated by a physician on paper and then scanned. Such template schematic representation may comprise a barcode or other type of image-based code identifying the particular template schematic representation, which may then be detected by the system.

Optionally, the second image data is volumetric image data, and set of instructions cause the processor to:
- determine a geometry of the view of the anatomical structure in the schematic representation; and
- generate the output image to show the anatomical structure in the second image data in accordance with said determined geometry.

The schematic representation may show the anatomical structure from a particular viewpoint which may be identified by the system, e.g., in any of the previously enumerated ways. In case the second image data is volumetric image data, this viewpoint may effectively be 'reproduced' in the output image by suitably processing the second image data. For example, multi-planar reformatting, intensity projection or volume rendering may be applied to the second image data to obtain an output image showing the anatomical structure from a same or similar viewpoint as is provided by the schematic representation of the anatomical structure.

Optionally, the set of instructions cause the processor to:
- via the input interface, access model data defining a segmentation model for segmenting the type of anatomical structure, the segmentation model comprising a set of anatomical landmarks;
- apply the segmentation model to the second image data, thereby obtaining a patient-adapted segmentation model comprising a patient-adapted set of anatomical landmarks; and
- determine the view to be shown of the anatomical structure in the output image based on the patient-adapted set of anatomical landmarks.

To enable the system to show a view of the anatomical structure of the second image data which resembles the view provided by the schematic representation, the system may identify the anatomical structure in the second image data rather than, for example, simply assuming a particular location, orientation, etc. of the anatomical structure. For that purpose, a segmentation technique may be used, for example, model-based segmentation. Segmentation models comprising anatomical landmarks are known per se. Such a segmentation model may be applied to the second image data so as to adapt the segmentation model to the particular anatomical structure shown therein, e.g., to obtain a patient-adapted segmentation model. This may provide the system with the position, orientation and/or shape of the anatomical structure, on which basis a desired view of the anatomical structure in the second image data may be generated.

Optionally, the second image data comprises a time-series of images representing an anatomical cycle of the anatomical structure, wherein set of instructions cause the processor to:
- determine which part of the anatomical cycle is shown by the view of the anatomical structure in the schematic representation; and
- generate the output image to show the anatomical structure in the second image data in accordance with said determined part of the anatomical cycle.

Alternatively or additionally to reproducing a particular viewpoint in the output image, the system may identify which part of an anatomical cycle is shown by the view of the anatomical structure in the schematic representation, and select a corresponding part of the second image data for inclusion in the output image. For example, in case the anatomical structure is a heart, the anatomical cycle may be the heart cycle and the phase of the heart cycle shown in the schematic representation may be reproduced in the output image. Another example may be the selection of a time instance when a pathology may be seen best, e.g., because of contrast agent by which a stenosis is visible.

Alternatively or additionally, the medical image data of the patient may comprise a 2D image or a series of 2D images, e.g., an 2D image sequence, which shows a particular view of the anatomical structure. In the example of the heart, different views may be acquired which may include 2 chamber views, 3 chamber views, 4 chamber views, short axis views, long axis views, etc. It is customary for many of these 'standard' 2D images or image sequences to be acquired for one patient. Accordingly, the identification of the view may pertain to identifying an 2D image or 2D image sequence which corresponds, in terms of provided view, to the schematic representation.

It will be appreciated by those skilled in the art that two or more of the above-mentioned embodiments, implementations, and/or optional aspects of the invention may be combined in any way deemed useful.

Modifications and variations of the workstation, the imaging apparatus, the method and/or the computer program product, which correspond to the described modifications and variations of the system, can be carried out by a person skilled in the art on the basis of the present description.

A person skilled in the art will appreciate that the system and method may be applied to image data acquired by various acquisition modalities such as, but not limited to, standard X-ray Imaging, Computed Tomography (CT), Magnetic Resonance Imaging (MRI), Ultrasound (US), Positron Emission Tomography (PET), Single Photon Emission Computed Tomography (SPECT), and Nuclear Medicine (NM).

BRIEF DESCRIPTION OF THE DRAWINGS

These and other aspects of the invention will be apparent from and elucidated further with reference to the embodiments described by way of example in the following description and with reference to the accompanying drawings, in which.

It should be noted that the figures are purely diagrammatic and not drawn to scale. In the figures, elements which correspond to elements already described may have the same reference numerals.

LIST OF REFERENCE NUMBERS

The following list of reference numbers is provided for facilitating the interpretation of the drawings and shall not be construed as limiting the claims.
020 image data repository
022 data communication
030 first image data
032 second image data
060 display
062 display data
080 user input device
082 user input data
100 system for display of medical image data
120 input interface
122 internal data communication
140 processor
142 internal data communication
144 internal data communication
160 memory
180 user interface subsystem
182 display output interface
184 user input interface
200 section from a medical report
210 schematic representation of coronary arterial tree
212 schematic representation of mouth and throat
220 annotation in schematic representation
300 image volume of volumetric image data
310 view plane
320 output image generated from volumetric image data
330 annotation in output image
400 segmentation model of the heart
500 method for displaying medical image data
510 accessing image data of schematic representation
520 determining type and view of anatomical structure
530 accessing medial image data
540 generating output image
600 computer-readable medium
610 non-transitory data

DETAILED DESCRIPTION OF EMBODIMENTS

Figure 1:
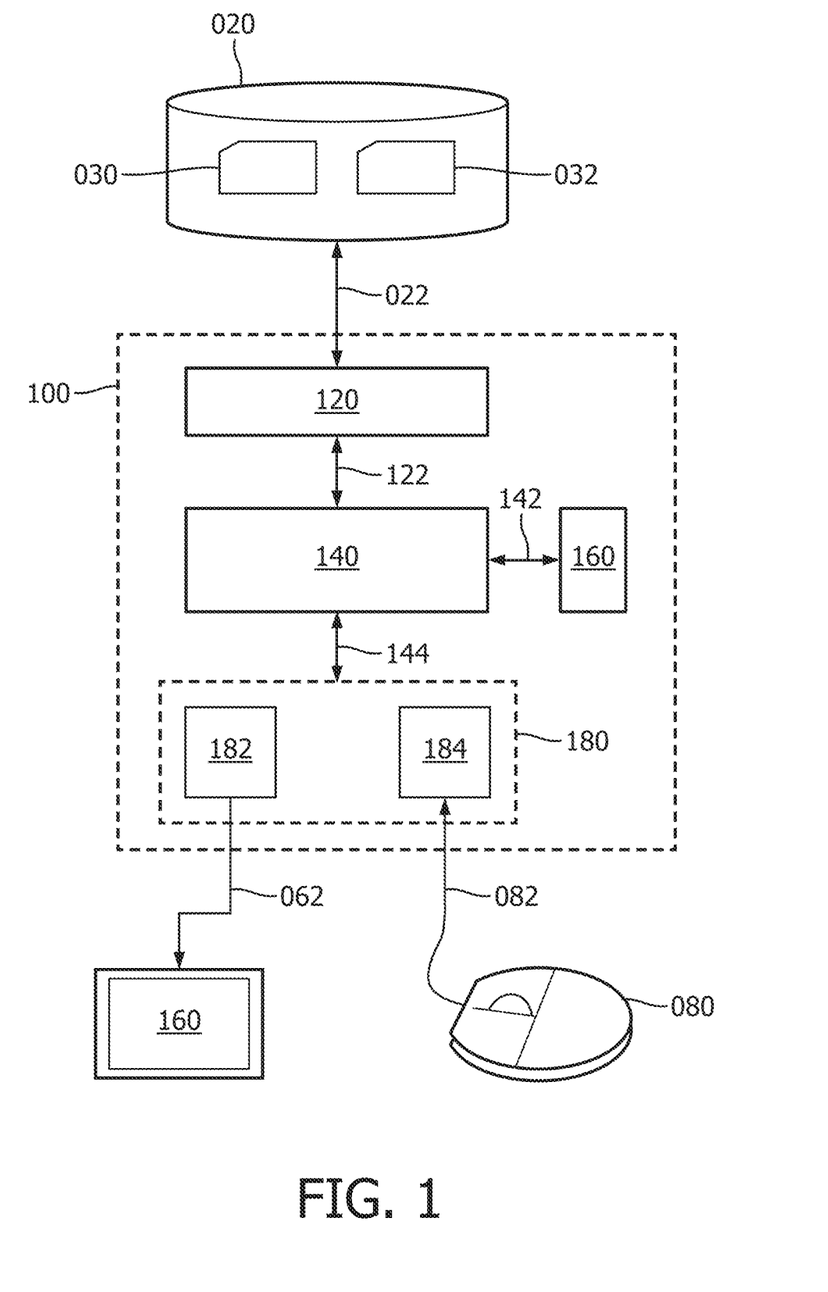
FIG. 1 shows a system for display of medical image data, to which a display and a user input device is connected.

FIG. 1 shows a system 100 for display of medical image data. The system 100 comprises an input interface 120 configured to access image data. In the example of FIG. 1, the input interface 120 is shown to be connected to an external image repository 020 which comprises first image data 030 comprising a schematic representation of an anatomical structure and second image data 032 acquired of a patient. The image repository 020 may, for example be constituted by, or be part of, a Picture Archiving and Communication System (PACS) of a Hospital Information System (HIS) to which the system 100 may be connected or comprised in. Accordingly, the system 100 may obtain access to the image data 030, 032 via external data communication 022. Alternatively, the image data 030, 032 may be accessed from an internal data storage of the system 100 (not shown).

In general, the first image data 030 and the second image data 032 may be accessed from a same location, e.g., a same image repository as in the case of FIG. 1, but also from different locations, e.g., from different image repositories.

In general, the input interface 120 may take various forms, such as a network interface to a local or wide area network, e.g., the Internet, a storage interface to an internal or external data storage, etc.

The system 100 is further shown to comprise a processor 140 configured to internally communicate with the input interface 120 via data communication 122, and a memory 160 accessible by the processor 140 via data communication 142. The processor 140 is further shown to internally communicate with a user interface subsystem 180 via data communication 144.

The processor 140 may be configured to, during operation of the system 100, analyze the first image data to determine i) a type of anatomical structure and ii) the view of the anatomical structure provided by the schematic representation, based on one or more image features in the first image data. Moreover, the processor 140 may be configured to, via the input interface 120, access second image data acquired of a patient, the second image data comprising the type of anatomical structure, and to generate an output image showing the anatomical structure in the second image data in accordance with said determined view.

This operation of the system 100, and various optional aspects thereof, will be explained in more detail with reference to FIGS. 2-4.

FIG. 1 also shows various optional system components. For example, for interactive image viewing, the system 100 may comprise a user interface subsystem 180 which may be configured to, during operation of the system 100, enable a user to interact with the system 100, for example using a graphical user interface. The user interface subsystem 180 is shown to comprise a user input interface 184 configured to receive user input data 082 from a user input device 080 operable by the user. The user input device 080 may take various forms, including but not limited to a computer mouse, touch screen, keyboard, microphone, etc. FIG. 1 shows the user input device to be a computer mouse 080. In general, the user input interface 184 may be of a type which corresponds to the type of user input device 080, i.e., it may be a thereto corresponding type of user device interface 184.

The user interface subsystem 180 is further shown to comprise a display output interface 182 configured to provide display data 062 to a display 060 to visualize output of the system 100. In the example of FIG. 1, the display is an external display 060. Alternatively, the display may be an internal display.

In general, the system 100 may be embodied as, or in, a single device or apparatus, such as a workstation or imaging apparatus or mobile device. The device or apparatus may comprise one or more microprocessors which execute appropriate software. The software may have been downloaded and/or stored in a corresponding memory, e.g., a volatile memory such as RAM or a non-volatile memory such as Flash. Alternatively, the functional units of the system, e.g., the input interface, the optional user input interface, the optional display output interface and the processor, may be implemented in the device or apparatus in the form of programmable logic, e.g., as a Field-Programmable Gate Array (FPGA). In general, each functional unit of the system may be implemented in the form of a circuit. It is noted that the system 100 may also be implemented in a distributed manner, e.g., involving different devices or apparatuses. For example, the distribution may be in accordance with a client-server model, e.g., using a server and a thin-client.

Figure 2:
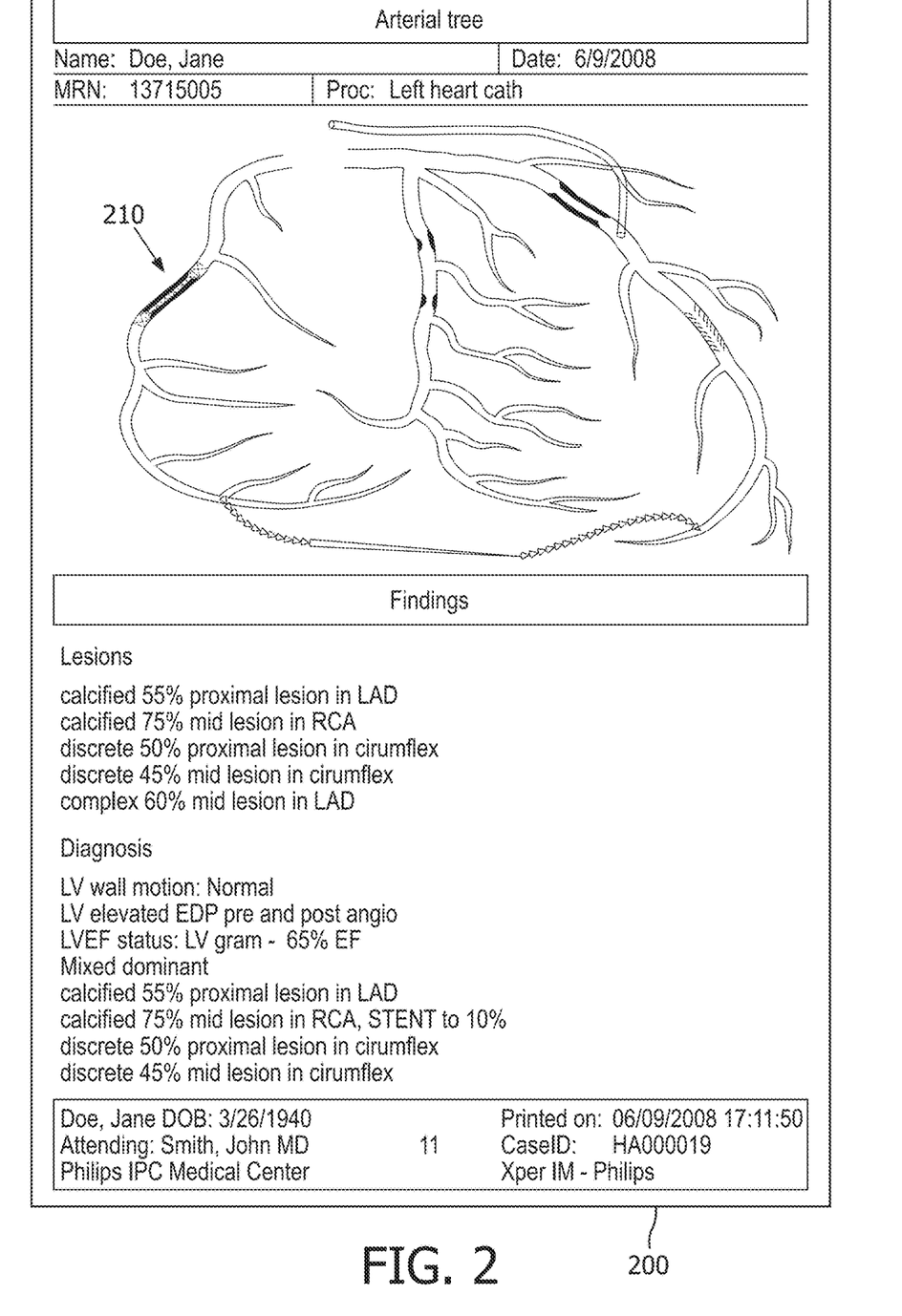
FIG. 2 show a section of a medical report of a patient which includes a schematic representation of the coronary arterial tree.

FIG. 2 show a section of a medical report 200 of a patient which includes a schematic representation 210 of the coronary arterial tree. Such schematic representations of anatomical structures are frequently used in medical reporting, and may be used to indicate, by way of annotation, anatomical regions of interest, e.g., medical abnormalities. Conventionally, such a schematic representation 210 may be provided on paper and subsequently scanned or photographed, e.g., with a smartphone. In general, the annotation may be applied on paper and/or to the (digital) image data of the schematic representation.

Figure 3A:
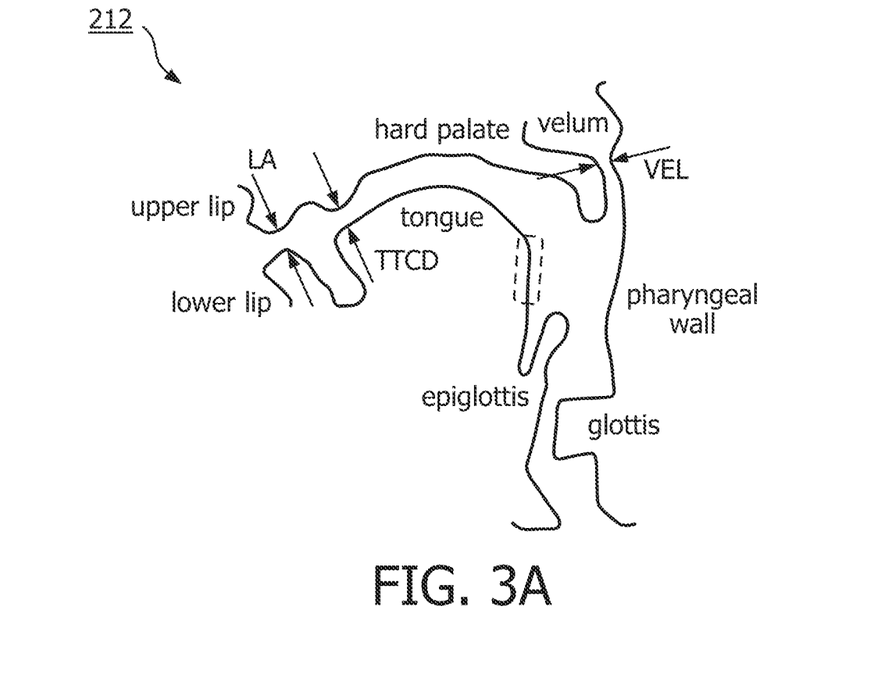
FIG. 3A shows a schematic representation of the mouth and throat, with the schematic representation comprising an annotation.
Figure 3B:
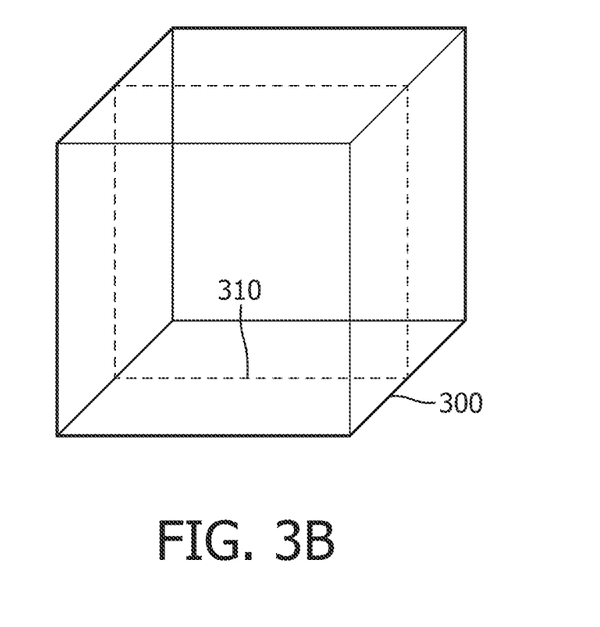
FIG. 3B shows an image volume representing volumetric image data of the mouth and throat of a patient, and a view plane which provides a corresponding view of the mouth and throat as the schematic representation of FIG. 3A.
Figure 3C:
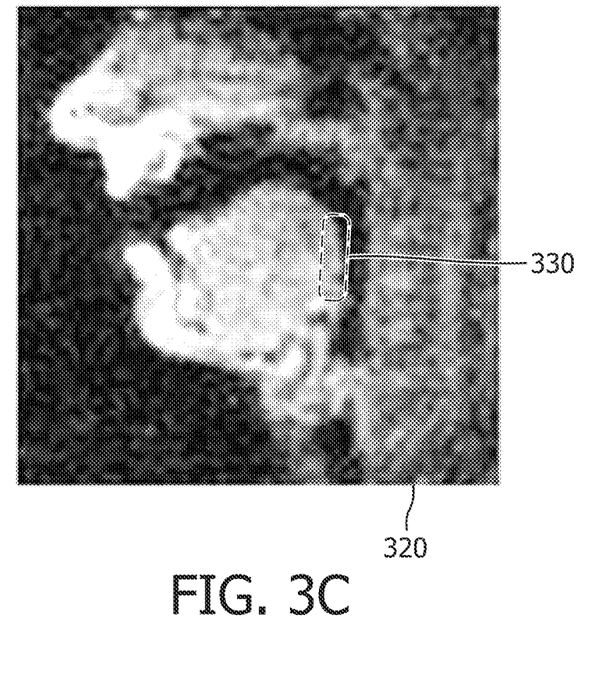
FIG. 3C shows an output image which is generated of the volumetric image data in accordance with the view plane of FIG. 3B.
Figure 4:
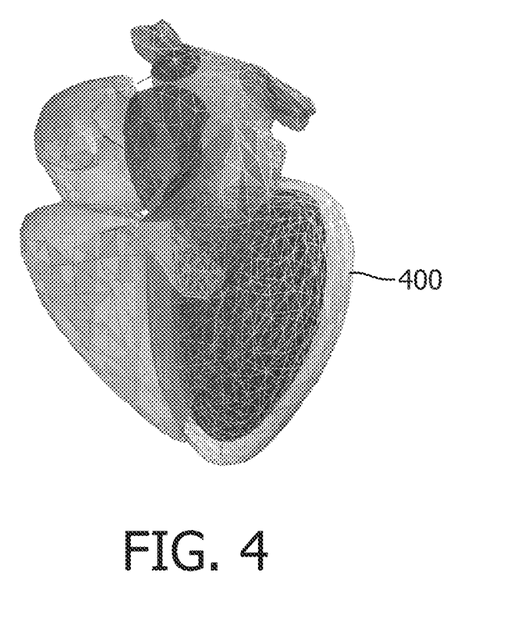
FIG. 4 shows a segmentation model, being in this example of the heart, which may be used to identify the location, orientation and/or shape of an anatomical structure in medical image data of a patient.

The following first provides a brief explanation of an operation of the system with reference to FIGS. 3A-3C. Thereafter, a more detailed explanation is provided with continued reference to FIGS. 3A-3C as well as FIG. 4.

FIG. 3A shows another example of a schematic representation 212 of an anatomical structure, being in this example the mouth and throat. In this example, an annotation 220 has been applied to the schematic representation to mark an anatomical region of interest, e.g., a medical abnormality. The image data of such a schematic presentation may be accessed and analyzed by the system to determine a type of anatomical structure and the view of the anatomical structure provided by the schematic representation, e.g., in a manner as elucidated further onwards.

The system may further access second image data acquired of a patient which comprises the type of anatomical structure. In some embodiments, the second image data may be volumetric image data, which may be schematically represented by a rectangular image volume 300 as shown in FIG. 3B.

The system may then generate an output image showing the anatomical structure in the second image data in accordance with said determined view. For example, the system may have determined that the schematic representation of FIG. 3A represents a sagittal cross-section of the mouth and throat. The system may have also determined that such a sagittal cross-section corresponds to a view plane 310 intersecting the image volume 300. An output image may then be generated by the system, e.g., using multiplanar reformatting, yielding an output image 320 as shown in FIG. 3C. Optionally, the system may insert an annotation 330 in the output image 320 at substantially the same anatomical location as is present in the schematic representation of FIG. 3A.

With continued reference to FIG. 3A, it is noted that the type of anatomical structure and the view of the anatomical structure may be determined by the system in various ways. For example, the system may access a database containing the image data of a set of schematic representations of anatomical structures and metadata indicating for each schematic representation the type of anatomical structure. The schematic representations in the database are also referred to as 'reference' schematic representations. The database may be the same but also a different database than the database(s) containing the first image data and/or the second image data, e.g., the image repository 120 of FIG. 1.

It may then be determined which one of the schematic representations from the database best matches the current schematic representation, e.g., by using an image registration technique and correspondence criteria as known per se in the fields of image registration and image analysis/processing. A specific example is than a rigid image registration technique may be used and that the correspondence may be quantified by an image similarity metric such as the sum of square distances, with the 'distance' being the difference between intensity values of both registered images. Various other image registration techniques and/or image similarity metrics are equally conceivable. The presence and location of an annotation, such as annotation 220 in FIG. 3A, may be determined from a simple difference image obtained from subtracting one registered image from the other. Alternatively, the annotation may be detected, e.g., on the basis of the annotation having a distinct visual property, such as a distinct color, shape, contour width, etc.

It is noted that the comparison to a database of reference schematic representations may be well suited for standardized schematic representations, in which case one of the reference schematic representations is expected to correspond to the current schematic representation. However, even in such a case, image registration may still be useful since the current schematic representation may have been translated, scaled, rotated or in another manner transformed in the image data with respect to the corresponding reference, e.g., due to scanning, a photograph being taken of a paper-based representation at an oblique angle, etc.

Alternatively or additionally to comparing the current schematic representation to a database of reference schematic representations, the schematic representation may be provided with an image-based code which identifies the type of anatomical structure, e.g., "Mouth and Throat", and the view provided by the schematic representation, e.g., "Sagittal cross-sectional", or at least allows these to be determined, e.g., based on a look-up in a database. An example of the latter is that the image-based code may provide an identifier of the schematic representation, e.g., "CSCV1", on the basis of which the type of anatomical structure and the view may be looked-up in a database, e.g., "Mouth and Throat" and "Sagittal cross-section". In general, the image-based code may be a barcode, a QR code, a numeric code, a text-based code, etc. An example of the latter is a figure heading or labels of anatomical landmarks, which may also be considered image-based code by the system, e.g., involving the use of optical character recognition (OCR) to convert the image-based representation of the text into a character-based representation.

Alternatively or additionally to the above approaches, the type of anatomy and the view may be determined by image classification techniques. For example, a machine learning technique may be used, such as deep learning. Such image classification may involve pre-processing, e.g., a thresholding of the first image data to identify contours of the anatomical structure, with the thresholded image data then being used as input to the image classification technique. It will be appreciated that image classification is known per se, and it will be within reach of the skilled person to select and configure an image classification technique to determine the type of anatomical structure as well as the view, e.g., the viewpoint from which the anatomical structure is shown in the schematic representation.

A specific example of the latter, e.g., the determining of the view and specifically the viewpoint, may involve deep-learning, e.g., based on convolutional neural networks, which may be trained as follows. A 3D model of the anatomical structure may be accessed. For example, the 3D model may be a segmentation model for segmenting a type of anatomical structure. Then, projections of the 3D model may be generated from different viewpoints, thereby obtaining a set of 2D images. The 2D images may then be used as training input to the deep learning, together with data characterizing the viewpoint from which the projection is created, e.g., the projection origin, or in case of an orthogonal projection, a viewpoint which is located at a distance from the anatomical structure along a central projection vector.

Optionally, negative examples may be included in the training, e.g., schematic representations of different anatomical structures. In an iterative optimization process, e.g., using backpropagation, the convolutional neural network may be optimized in order to reliably predict the viewpoint from the image data of the schematic representation. It is noted that such training may be performed for different types of anatomical structures, either by training a single convolutional neural network to also classify the type of anatomical structure, or by training separate convolutional networks for different types of anatomical structures.

With continued reference to FIGS. 3B and 3C, a view may be generated from the medical image data of the patient in various ways. For example, if the medical image data is volumetric image data, the system may determine a geometry of the view of the anatomical structure in the schematic representation, and generate the output image to show the anatomical structure in the second image data in accordance with said determined view geometry. In this respect, it is noted that a viewpoint or view geometry may be defined by the same or similar parameters as is known per se from 'virtual cameras', e.g., by a translation vector and an orientation vector. Alternatively, the viewpoint or view geometry may be defined as a view plane intersecting the image volume, e.g., an intersection plane or projection plane.

In general, volumetric image data may be acquired by medical image acquisition techniques such as Computed Tomography (CT), Magnetic Resonance (MR), etc. Here, the term 'volumetric image data' refers to image data which represents an image volume. Such volumetric image data may provide a three-dimensional (3D) view of an anatomical region or structure of the patient, and may thereby support medical diagnosis and treatment of the patient.

Depending on the type of medical image data and the type of viewpoint or view geometry (e.g., intersection or exterior view of the anatomical structure), the output image may be generated in various ways. For example, if the volumetric image data is represented by a stack of image slices, one of the image slices may be selected for display in case of an intersection plane. Another example is that an oblique slice may be generated using a multi-planar reformatting technique.

Yet another example is that a volume rendering technique be used to generate a two-dimensional (2D) view of the volumetric image data. Several volume rendering techniques are known in the art, which may generally involve assigning opacity values to the image data and projecting the image data onto a viewing plane using the opacity values. The output of volume rendering is typically a 2D image.

It is noted that the system may be aware of the location and orientation of the anatomical structure in the medical image data, e.g., by this being standardized or indicated by metadata, such as a DICOM Tag or a filename. Additionally or alternatively, segmentation, such as model-based segmentation, may be used to determine the location, orientation and/or shape of the anatomical structure in the medical image data of a patient. Namely, a segmentation model may be applied to the medical image data, as known per se in the field of model-based segmentation and described in, e.g., "*Automatic Model-based Segmentation of the Heart in CT Images*" by Ecabert et al., IEEE Transactions on Medical Imaging 2008, 27(9), pp. 1189-1201, thereby obtaining a patient-adapted segmentation model. FIG. 4 shows an example of such a segmentation model, being a cardiac model.

Since such a segmentation model typically comprises anatomical landmarks, the patient's anatomical landmarks are now known from the applied segmentation model, which provides the system with information on the location, orientation and shape of the anatomical structure in the medical image data. Such information may be used when generating the output image. For example, if an intersectional view is to be generated of the medical image data, the intersection plane may be positioned at the correct anatomical position within the image volume.

In general, the system may annotate the output image in correspondence with an annotation in the schematic representation. Alternatively, the schematic representation, including its annotation, may be overlaid in the output image over the visualization of the medical image data of the patient.

In general, the system may be a medical workstation for viewing medical images, e.g., for various types of image modalities.

Figure 5:
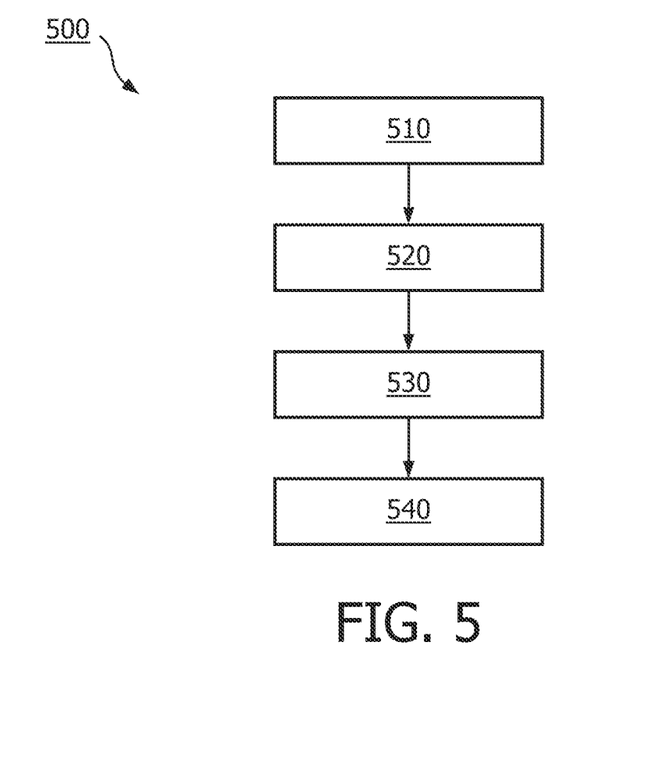
FIG. 5 shows a block-diagram of a computer-implemented method for display of medical image data.

FIG. 5 shows a computer-implemented method 500 for display of medical image data. It is noted that the method 500 may, but does not need to, correspond to an operation of the system 100 as described with reference to FIG. 1 and others. The method 500 comprises, in an operation titled "ACCESSING IMAGE DATA OF SCHEMATIC REPRESENTATION", accessing 510 first image data comprising a schematic representation of an anatomical structure, the schematic representation providing a particular view of the anatomical structure. The method 500 further comprises, in an operation titled "DETERMINING TYPE AND VIEW OF ANATOMICAL STRUCTURE", analyzing 520 the first image data to determine i) a type of anatomical structure and ii) the view of the anatomical structure provided by the schematic representation, based on one or more image features in the first image data. The method 500 further comprises, in an operation titled "ACCESSING MEDIAL IMAGE DATA", accessing 530 second image data acquired of a patient, the second image data comprising the type of anatomical structure. The method 500 further comprises, in an operation titled "GENERATING OUTPUT IMAGE", generating 540 an output image showing the anatomical structure in the second image data in accordance with said determined view. It will be appreciated that, in general, the above operations may be performed in any suitable order, e.g., consecutively, simultaneously, or a combination thereof, subject to, where applicable, a particular order being necessitated, e.g., by input/output relations.

Figure 6:
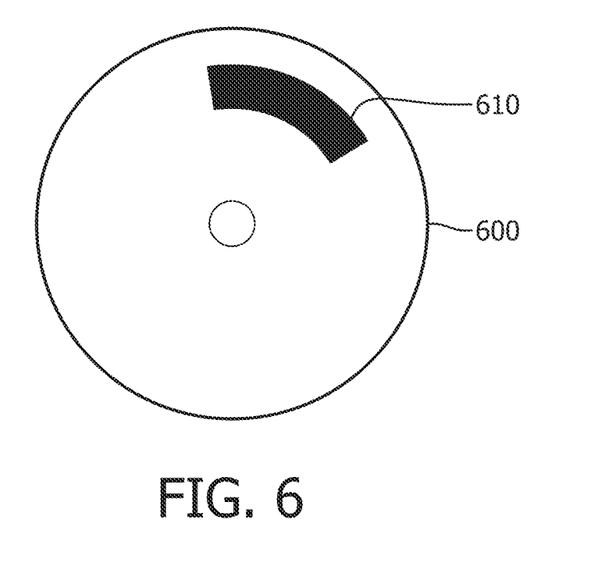
FIG. 6 shows a computer-readable medium comprising instructions for causing a processor system to perform the method.

The method 500 may be implemented on a computer as a computer implemented method, as dedicated hardware, or as a combination of both. As also illustrated in FIG. 6, instructions for the computer, e.g., executable code, may be stored on a computer readable medium 600, e.g., in the form of a series 610 of machine readable physical marks and/or as a series of elements having different electrical, e.g., magnetic, or optical properties or values. The executable code may be stored in a transitory or non-transitory manner. Examples of computer readable mediums include memory devices, optical storage devices, integrated circuits, servers, online software, etc. FIG. 6 shows an optical disc 600.

In accordance with an abstract of the present application, a system and method may be provided for display of medical image data, with the display of the medical image data being determined on the basis of schematic image data of a schematic representation of an anatomical structure. The schematic representation may provide a particular view of the anatomical structure. The type of anatomical structure and the view of the anatomical structure provided by the schematic representation may be determined based on one or more image features in the schematic image data. An output image may be generated showing the anatomical structure in the medical image data in accordance with said determined view. A user may thus be provided with a display of medical image data which is easier to interpret having considered said schematic representation.

Examples, embodiments or optional features, whether indicated as non-limiting or not, are not to be understood as limiting the invention as claimed.

It will be appreciated that the invention also applies to computer programs, particularly computer programs on or in a carrier, adapted to put the invention into practice. The program may be in the form of a source code, an object code, a code intermediate source and an object code such as in a partially compiled form, or in any other form suitable for use in the implementation of the method according to the invention. It will also be appreciated that such a program may have many different architectural designs. For example, a program code implementing the functionality of the method or system according to the invention may be sub-divided into one or more sub-routines. Many different ways of distributing the functionality among these sub-routines will be apparent to the skilled person. The sub-routines may be stored together in one executable file to form a self-contained program. Such an executable file may comprise computer-executable instructions, for example, processor instructions and/or interpreter instructions (e.g. Java instructions). Alternatively, one or more or all of the sub-routines may be stored in at least one external library file and linked with a main program either statically or dynamically, e.g. at run-time. The main program contains at least one call to at least one of the sub-routines. The sub-routines may also comprise function calls to each other. An embodiment relating to a computer program product comprises computer-executable instructions corresponding to each processing stage of at least one of the methods set forth herein. These instructions may be sub-divided into sub-routines and/or stored in one or more files that may be linked statically or dynamically. Another embodiment relating to a computer program product comprises computer-executable instructions corresponding to each means of at least one of the systems and/or products set forth herein. These instructions may be sub-divided into sub-routines and/or stored in one or more files that may be linked statically or dynamically.

The carrier of a computer program may be any entity or device capable of carrying the program. For example, the carrier may include a data storage, such as a ROM, for example, a CD ROM or a semiconductor ROM, or a magnetic recording medium, for example, a hard disk. Furthermore, the carrier may be a transmissible carrier such as an electric or optical signal, which may be conveyed via electric or optical cable or by radio or other means. When the program is embodied in such a signal, the carrier may be constituted by such a cable or other device or means. Alternatively, the carrier may be an integrated circuit in which the program is embedded, the integrated circuit being adapted to perform, or used in the performance of, the relevant method.

It should be noted that the above-mentioned embodiments illustrate rather than limit the invention, and that those skilled in the art will be able to design many alternative embodiments without departing from the scope of the appended claims. In the claims, any reference signs placed between parentheses shall not be construed as limiting the claim. Use of the verb "comprise" and its conjugations does not exclude the presence of elements or stages other than those stated in a claim. The article "a" or "an" preceding an element does not exclude the presence of a plurality of such elements. The invention may be implemented by means of hardware comprising several distinct elements, and by means of a suitably programmed computer. In the device claim enumerating several means, several of these means may be embodied by one and the same item of hardware. The mere fact that certain measures are recited in mutually different dependent claims does not indicate that a combination of these measures cannot be used to advantage.

The invention claimed is:

1. A system for display of medical image data, comprising:
    an input interface for accessing first image data comprising a schematic representation of an anatomical structure, the schematic representation providing a particular view of the anatomical structure;
a memory comprising instruction data representing a set of instructions;
a processor configured to communicate with the input interface and the memory and to execute the set of instructions, wherein the set of instructions, when executed by the processor, cause the processor to:
analyze the first image data to determine i) a type of anatomical structure and ii) the view of the anatomical structure provided by the schematic representation, by applying an image classification technique to the first image data and based on one or more image features in the first image data, the view being characterized as a geometrically-defined perspective at which the anatomical structure is shown in the schematic representation, wherein the image classification technique is trained to identify a view provided by the schematic representation by:
accessing a 3D model of the type of anatomical structure;
generating projections of the 3D model from different viewpoints, thereby obtaining a set of 2D images; and
using the 2D images and data characterizing the different viewpoints as training input to the image classification technique;
via the input interface, access second image data being volumetric image data acquired of a patient, the second image data comprising the type of anatomical structure; and
generate an output image showing the anatomical structure in the second image data in accordance with said geometrically-defined perspective.

2. The system according to claim 1, wherein the schematic representation of the anatomical structure comprises an annotation, and wherein the set of instructions cause the processor to:
detect an anatomical location of the annotation in the schematic representation of the anatomical structure; and
based on said detected anatomical location, annotate the output image in correspondence with the annotation in the schematic representation.

3. The system according to claim 1, wherein the set of instructions cause the processor to determine the type of anatomical structure and/or the view of the anatomical structure by:
via the input interface, accessing a database comprising i) image data of a set of schematic representations of anatomical structures and ii) metadata indicating for each schematic representation the type of anatomical structure and/or the view of the anatomical structure provided by the respective schematic representation; and
comparing the first image data to the image data of each, or a subset of the set of schematic representations.

4. The system according to claim 3, wherein said comparing comprises:
registering the first image data to the image data of each, or the subset of the set of schematic representations, and
determining a correspondence of said registered image data.

5. The system according to claim 1, wherein the image classification technique is based on machine learning and the 3D model comprises a segmentation model.

6. The system according to claim 1, wherein the first image data comprises an image-based code indicative of the type of anatomical part and/or the view of the anatomical structure provided by the schematic representation, wherein the set of instructions cause the processor to analyze the first image data to identify the image-based code.

7. The system according to claim 1, wherein the set of instructions cause the processor to further characterize the view as a type of view provided by the schematic representation and to generate the output image in accordance with the type of view.

8. The system according to claim 1, wherein the set of instructions cause the processor to generate the output image using at least one: multi-planar reformatting, intensity projection and volume rendering.

9. The system according to claim 1, wherein the set of instructions cause the processor to:
via the input interface, access model data defining a segmentation model for segmenting the type of anatomical structure, the segmentation model comprising a set of anatomical landmarks;
apply the segmentation model to the second image data, thereby obtaining a patient-adapted segmentation model comprising a patient-adapted set of anatomical landmarks; and
determine the view to be shown of the anatomical structure in the output image based on the patient-adapted set of anatomical landmarks.

10. The system according to claim 1, wherein the second image data comprises a time-series of images representing an anatomical cycle of the anatomical structure, wherein set of instructions cause the processor to:
determine which part of the anatomical cycle is shown by the view of the anatomical structure in the schematic representation; and
generate the output image to show the anatomical structure in the second image data in accordance with said determined part of the anatomical cycle.

11. A workstation or imaging apparatus comprising the system according to claim 1.

12. A computer-implemented method for display of medical image data, comprising:
accessing first image data comprising a schematic representation of an anatomical structure, the schematic representation providing a particular view of the anatomical structure;
analyzing the first image data to determine i) a type of anatomical structure and ii) the view of the anatomical structure provided by the schematic representation, by applying an image classification technique to the first image data and based on one or more image features in the first image data, the view being characterized as a geometrically-defined perspective at which the anatomical structure is shown in the schematic representation, wherein the image classification technique is trained to identify a view provided by the schematic representation by:
accessing a 3D model of the type of anatomical structure;
generating projections of the 3D model from different viewpoints, thereby obtaining a set of 2D images; and
using the 2D images and data characterizing the different viewpoints as training input to the image classification technique;
accessing second image data being volumetric image data acquired of a patient, the second image data comprising the type of anatomical structure; and generating an output image showing the anatomical structure in the second image data in accordance with said geometrically-defined perspective.

13. A non-transitory computer-readable medium storing instructions that, when executed by one or more processors, cause the one or more processors to:

access first image data comprising a schematic representation of an anatomical structure, the schematic representation providing a particular view of the anatomical structure;

analyze the first image data to determine i) a type of anatomical structure and ii) the view of the anatomical structure provided by the schematic representation, by applying an image classification technique to the first image data and based on one or more image features in the first image data, the view being characterized as a geometrically-defined perspective at which the anatomical structure is shown in the schematic representation, wherein the image classification technique is trained to identify a view provided by the schematic representation by:

accessing a 3D model of the type of anatomical structure;

generating projections of the 3D model from different viewpoints, thereby obtaining a set of 2D images; and using the 2D images and data characterizing the different viewpoints as training input to the image classification technique;

access second image data being volumetric image data acquired of a patient, the second image data comprising the type of anatomical structure; and generate an output image showing the anatomical structure in the second image data in accordance with said geometrically-defined perspective.

* * * * *